United States Patent [19]

Clitherow

[11] Patent Number: 5,273,984

[45] Date of Patent: * Dec. 28, 1993

[54] SALTS FORMED BETWEEN BASIC HISTAMINE $H_2$-RECEPTOR ANTAGONISTS AND BISMUTH COMPLEXES

[75] Inventor: John W. Clitherow, Sawbridgeworth, England

[73] Assignee: Glaxo Group Limited, London, England

[*] Notice: The portion of the term of this patent subsequent to Apr. 16, 2008 has been disclaimed.

[21] Appl. No.: 426,239

[22] Filed: Oct. 25, 1989

[30] Foreign Application Priority Data

Oct. 26, 1988 [GB] United Kingdom ............... 88 25058
Jun. 26, 1989 [GB] United Kingdom ............... 89 14631

[51] Int. Cl.$^5$ ..................... A61K 31/415; C07F 9/94; C07D 211/52; C07D 233/54; C07D 277/20
[52] U.S. Cl. ..................... 514/340; 514/399; 514/400; 514/439; 546/5; 546/6; 546/210; 548/106; 548/205; 548/335.5
[58] Field of Search ..................... 548/344, 106, 335.5; 514/399, 340, 400, 439; 546/210, 5, 6

[56] References Cited

U.S. PATENT DOCUMENTS 5,008,256  4/1991  Clitherow ........................... 514/184

FOREIGN PATENT DOCUMENTS 0282131  9/1988  European Pat. Off. ............ 548/344
0282132  9/1988  European Pat. Off. ............ 548/344

OTHER PUBLICATIONS

S. J. Konturek et al., *Gut*, 1987, 28, pp. 1557–1563.
S. J. Konturek et al., *Scandinavian Journal of Gastroenterology* 1987, 22, pp. 1059–1063.
R. Iserhard et al., Abstract of a paper given at the 20th Congress of the European Assoc. of Gastroenterology and Endoscopy, Apr. 28–30, 1988.
Lancet, (M. Guslandi, 1988, (8599), pp. 1383–1385).
M. V. Borkent et al., *Gut*, 1988, 29, pp. 385–389.
British Pharmaceutical Codex, 1949, "Bismuthi Carbonas" p. 150.
Salmon, P. R., *Digestion*, 1987, 37 (suppl. 2), 42–46.
British Pharmaceutical Codex, 1949, "Busmuthi Carbonas" 150–154 and 1183–1185.
Ward et al., *Proc. Adelaide*, 1979, A30 (Abstract).
Bianchi Porro et al., *Scandinavian Journal of Gastroenterology*, 21, supplement 122, 1986, 39–41.
Lam et al., *Gut*, 1984, 25, 703–706.

*Primary Examiner*—Floyd D. Higel
*Attorney, Agent, or Firm*—Bacon & Thomas

[57] ABSTRACT

The invention relates to salts formed between basic $H_2$-receptor antagonists and a complex of bismuth with a carboxylic acid, and solvates of such salts, excluding salts in which the basic $H_2$-receptor antagonist is ranitidine. Examples of suitable carboxylic acids are citric acid and tartaric acid. Examples of basic $H_2$-receptor antagonists are cimetidine, sufotidine famotidine and nizatidine.

The salts are useful in the treatment of gastrointestinal disorders, particularly gastroduodenal conditions. The salts show the antisecretory activity associated with the basic $H_2$-receptor antagonist together with antibacterial activity against Campylobacter pylori, and they also possess cytoprotective properties.

12 Claims, No Drawings

SALTS FORMED BETWEEN BASIC HISTAMINE H₂-RECEPTOR ANTAGONISTS AND BISMUTH COMPLEXES

This invention relates to salts of compounds having antagonist activity at histamine H2-receptors, to a process for the preparation thereof, to pharmaceutical compositions containing them and to their use in therapeutics. More particularly the invention is concerned with salts of histamine H2-receptor antagonists formed with bismuth complexes of carboxylic acids.

Compounds which have antagonist activity at histamine H2-receptors are used in the treatment of conditions where there is an advantage in lowering gastric acidity. Such conditions include duodenal and gastric ulceration, reflux oesophagitis and Zollinger-Ellison syndrome. H2-receptor antagonists may also be used prophylactically in surgical procedures, and in the treatment of allergic and inflammatory conditions where histamine is a known mediator.

Bismuth salts and preparations, such as bismuth citrate, bismuth and ammonium citrate, sodium bismuthyl tartrate, acid bismuth sodium tartrate, acid solution of bismuth, concentrated solution of bismuth, and solution of bismuth and ammonium citrate, which are described in for example the British Pharmaceutical Codex (1949), have long been used as antacids in the treatment of hyperacidity and dyspepsia. In addition, before the advent of histamine H2-antagonists, by which they have now essentially been superceded, such bismuth preparations were also used in the treatment of gastrointestinal ulcers.

In recent years evidence has emerged that *Campylobacter pylori* is associated with histological gastritis, non-ulcer dyspepsia and hypochlorhydria, and may be involved in the pathogenesis of gastric and duodenal ulcer disease.

*Campylobacter pylori* is susceptible to bismuth compounds such as bismuth subcitrate (in the form of, for example, tripotassium dicitrato bismuthate) and bismuth subsalicylate.

According to published European Patent Specification No. 282132, a bismuth-containing agent, preferably a campylobacter-inhibiting bismuth-containing agent such as bismuth subsalicylate or bismuth subcitrate, may be co-administered with a H2-receptor antagonist, preferably cimetidine or ranitidine, for the treatment of gastrointestinal disorders. The two active ingredients may be given as separate preparations which may be administered concurrently or non-concurrently, or may be contained in a single composition.

A number of the bismuth compounds described previously as antacids and/or agents for the inhibition of *Campylobacter pylori* are acidic complexes formed between bismuth and a carboxylic acid such as citric or tartaric acid or salts thereof with ammonia or an alkali metal.

It has now been found that basic H2-receptor antagonists will form salts with such complexes, and the resulting products possess a useful and advantageous profile of activity.

The present invention thus provides novel salts formed between a basic H2-receptor antagonist and a complex of bismuth with a carboxylic acid, and solvates of such salts. Suitable carboxylic acids are those which are capable of forming a complex with bismuth, and which complexes are, in turn, capable of forming a salt with the basic H2-antagonist. Salts in which the H2-receptor antagonist is ranitidine are however excluded from the scope of the invention.

Carboxylic acids which are capable of forming complexes with bismuth to give bismuth-carboxylic acid complexes for use according to the invention may be, for example, carboxylic acids which contain at least three functional groups in addition to the carboxyl group which is available for salt formation with the H2-receptor antagonist. Of the three or more remaining functional groups, three, which may be for example carboxyl and/or hydroxy groups, should be capable of complexing with trivalent bismuth, to give a trivalent bismuth complex.

In instances where the carboxylic acid can exhibit optical and/or geometric isomerism, the invention is intended to include all optical isomers including racemates, and/or geometric isomers. Solvates, including hydrates, are also included within the scope of the invention.

Examples of suitable carboxylic acids which are capable of forming complexes with bismuth for use according to the invention are citric, tartaric and ethylenediaminetetraacetic acids. Further examples of suitable carboxylic acids are propylcitric and agaricic acids. Tartaric acid and citric acid are preferred.

Suitable basic histamine H2-receptor antagonists for salt formation with bismuth-carboxylic acid complexes according to the invention include imidazole derivatives; substituted aminoalkylbenzene, furan and thiazole derivatives (e.g. dimethylaminomethyl-furanyl-methylthioethylamino compounds, piperidinomethyl-phenoxypropylamino compounds and dimethylaminomethylthiazolyl-methylthioethylamino compounds); guanidinothiazolyl derivatives including guanidinothiazolylmethylthioethyl and guanidinothiazolylmethylthioethylamino compounds; and guanidinopyrazolyl derivatives. Examples of particular basic histamine H2-receptor antagonists are cimetidine, sufotidine, famotidine, roxatidine, niperotidine, nizatidine, mifentidine, zaltidine, ebrotidine, bisfentidine, 1-methyl-5-[[3-[3-(1-piperidinylmethyl)phenoxy]propyl]amino]-1H-1,2,4-triazole-3-methanol, 3-amino-4-[[3-[3-(1-piperidinylmethyl)phenoxy]propyl]amino]-3-cyclobutene-1,2-dione (BMY 25368), and 5-[3-[2-(2,2,2-trifluoroethyl)guanidino]pyrazol-1-yl]valeramide.

Cimetidine and sufotidine represent preferred basic H2-receptor antagonists for use according to the invention. Another preferred basic H2-receptor antagonist for use according to the invention is famotidine. A further preferred basic H2-receptor antagonist for use according to the invention is nizatidine.

Preferred salts according to the invention are N-cyano-N'-methyl-N''-[2-[[(5-methyl-1H-imidazol-4-yl)methyl]thio]ethyl]guanidine 2-hydroxy-1,2,3-propanetricarboxylate bismuth (3+) complex (also known as cimetidine bismuth citrate), N-cyano-N'-methyl-N''-[2-[[(5-methyl-1H-imidazol-4-yl)methyl]thio]ethyl]guanidine [R-(R*R*)]-2,3-dihydroxybutanedioate bismuth (3+) complex (also known as cimetidine bismuth tartrate), and 1-methyl-3-methylsulphonylmethyl-N-[3-[3-(1-piperidinylmethyl)phenoxy]propyl]-1H-1,2,4-triazole-5-amine 2-hydroxy-1,2,3-propanetricarboxylate bismuth (3+) complex (also known as sufotidine bismuth citrate), of which cimetidine bismuth citrate is particularly preferred.

Another preferred salt according to the invention is 3-[[[2-[(aminoiminomethyl)amino]-4-thiazolyl]methyl]- thio]-N-(aminosulphonyl)propanimidamide 2-hydroxy-1,2,3-propanetricarboxylate bismuth (3+) complex (also known as famotidine bismuth citrate).

A further preferred salt according to the invention is N-[2-[[[2-[(dimethylamino)methyl]-4-thiazolyl]methyl]-thio]ethyl]-N'-methyl-2-nitro-1,1-ethenediamine 2-hydroxy-1,2,3-propanetricarboxylate bismuth (3+) complex (also known as nizatidine bismuth citrate).

The salts according to the invention possess a particularly advantageous combination of properties for the treatment of gastrointestinal disorders, especially peptic ulcer disease and other gastroduodenal conditions, for example gastritis and non-ulcer dyspepsia.

Salts according to the invention thus possess the $H_2$-antagonist antisecretory properties associated with the $H_2$-receptor antagonist, together with antibacterial activity against *Campylobacter pylori*. In addition, salts of the invention possess cytoprotective properties. They also display activity against the human gastric pepsins, with preferential inhibition of pepsin 1, a pepsin isozyme associated with peptic ulcer.

The antisecretory activity of compounds according to the invention may be demonstrated in vivo against histamine-induced gastric acid secretion in the Heidenhain pouch dog. The antibacterial activity of the salts against *Campylobacter pylori* and their ability to inhibit human pepsins have been demonstrated in vitro. Cytoprotective activity has been demonstrated in vivo by the ability of the salts to inhibit ethanol-induced gastric lesions in rats.

A further feature of the salts according to the invention is that they provide a means of increasing the solubility of bismuth under aqueous conditions. Under normal circumstances many bismuth salts and complexes, including those formed with carboxylic acids of the type used in forming salts of the invention, are insoluble. Bismuth citrate, for example, has a solubility (under neutral aqueous conditions) of only 0.2% on a weight to volume (w/v) basis, whereas the salts of the invention are significantly more soluble.

Thus the observed properties of salts according to the invention serve to emphasise the fact that they are distinct chemical entities which can be clearly distinguished from simple mixtures (e.g. admixtures of equimolar proportions) of the basic $H_2$-receptor antagonist and a complex formed between bismuth and a carboxylic acid.

Salts according to the invention may also be distinguished from simple mixtures of the basic $H_2$-receptor antagonist and a complex formed between bismuth and a carboxylic acid on the basis of infra-red spectroscopy.

Salts according to the invention may be prepared by reacting the $H_2$-receptor antagonist with an appropriate bismuth-carboxylic acid complex (e.g. bismuth citrate or bismuth ammonium citrate), in a suitable solvent such as water, and separating the salt thus formed from the mixture.

According to a further aspect the invention provides a salt formed between a basic $H_2$-receptor antagonist and a complex of bismuth with a carboxylic acid, including solvates of such salts, said salt being prepared by reacting the $H_2$-antagonist with a bismuth carboxylic acid complex.

The reaction between the $H_2$-receptor antagonist and an appropriate bismuth-carboxylic acid complex to give a salt according to the invention is preferably carried out at elevated temperature for example at a temperature within the range of 40° to 100° C. Once the reaction is complete (when, for example, the mixture has reached neutrality as judged by pH and/or dissolution is complete), the suspension or solution is cooled and filtered, and the required salt may be obtained from the filtrate, by evaporation followed by extraction and trituration of the resulting residue using for example an alcohol e.g. methanol or ethanol, a ketone e.g. acetone or an ether e.g. diethyl ether. Alternatively, the reaction mixture may be evaporated directly, followed by extraction and trituration of the resulting residue.

The intermediate bismuth-carboxylic acid complexes may in general be prepared by the procedures described in the British Pharmaceutical Codex (1949). Thus, for example, a suspension of a suitable bismuth salt (e.g. bismuth oxynitrate) and an appropriate carboxylic acid (e.g. citric or tartaric acid) in a solvent such as water may be heated at for example 90° to 100° C., the reaction being judged as complete when one drop of the mixture yields a clear solution when added to weak aqueous ammonia. The suspension is then optionally diluted with water, and the desired bismuth-carboxylic acid complex may be recovered by filtration.

Bismuth ammonium citrate may for example be prepared, in situ if desired, by treating bismuth citrate with an appropriate amount of aqueous ammonia.

The salts according to the invention may be formulated for administration in any convenient way and the invention includes within its scope pharmaceutical compositions containing a salt according to the invention adapted for use in human or veterinary medicine. Such compositions, which are primarily intended for oral administration, may be formulated in a conventional manner using one or more pharmaceutically acceptable carriers or excipients. Tablets represent a preferred type of composition.

For oral administration, the pharmaceutical compositions may take the form of, for example, tablets (including chewable or suckable tablets) or capsules. Such compositions may be prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

The dose at which the salts of the invention may be administered to man will depend upon the nature of the histamine $H_2$-receptor antagonist, and the salts may in general be administered at doses based on the normal dosage range at which the $H_2$-receptor antagonist concerned is therapeutically effective. Thus a suitable dosage of a salt of a bismuth-carboxylic acid complex in which the H$_2$-receptor antagonist is cimetidine may be for example 400 mg to 1.6 g per unit dose. Similarly, for famotidine 20 to 100 mg (more preferably 40 to 100 mg), for nizatidine 100 to 600 mg, for roxatidine 100 to 600 mg, for sufotidine 100 mg to 1.2 g, and for 1-methyl-5-[[3-[3-(1-piperidinylmethyl)phenoxy]propyl]amino -1H-1,2,4-triazole-3-methanol 10 to 400 mg (more preferably 30 to 400 mg).

The unit dose may be administered, for example, one to four times daily, preferably once or twice. The exact dose will depend on the nature and severity of the condition being treated. It will also be appreciated that it may be necessary to make routine variations to the dosage depending on the age and weight of the patient.

The invention is illustrated by the following Examples, in which temperatures are in ° C. System A as used for thin layer chromatography (t.l.c.) denotes dichloromethane:ethanol: 0.88 ammonia. T.l.c. was carried out on silica, and u.v., iodoplatinate and potassium permanganate were used for detection of the products.

PREPARATION 1

2-Hydroxy-1,2,3-propanetricarboxylic acid, bismuth (3+) complex (1:1) ("Bismuth citrate")

A mixture of bismuth oxynitrate (22.96 g) and citric acid (33.60 g) in water (80 ml) was heated on a steam bath with frequent stirring for 30 min, by which time one drop of the suspension added to weak aqueous ammonia gave a clear solution. The mixture was diluted with water, filtered, and the residue washed well with water until free of nitrate and excess citric acid. The residue was dried under vacuum to give the title compound (32.18 g).

Analysis Found: C,18.08; H,1.34; O, 28.80; Bi, 52. C$_6$H$_5$BiO$_7$. 0.11 H$_2$O requires C,18.01; H,1.32; O,28.44; Bi, 52.2%. Water assay indicated 0.49% H$_2$O=0.11 mol.

PREPARATION 2

[R-(R*R*)]-2,3-Dihydroxybutanedioic acid, bismuth (3+)complex (2:1) ("Bismuth tartrate")

A mixture of (+)-tartaric acid (27 g) and bismuth oxynitrate (8.61 g) in water (50 ml) was heated at 90°-100° with occassional stirring for 30 min, by which time a small portion of the product dissolved completely in weak aqueous ammonia. The mixture was cooled to room temperature then filtered and the filtrate washed well with water until free from water soluble materials. The residue was dried at 70°-80° in vacuo to give the title compound (14.78 g).

Analysis Found: C,18.44; H,1.81; O,39.04; Bi,40. C$_8$H$_9$Bi.O$_{12}$.0.43 H$_2$O requires C,18.70; H,1.93; O,38.70; Bi,40.7%. Water assay indicated 1.54% H$_2$O=0.43 mol H$_2$O.

EXAMPLE 1

N-Cyano-N'-methyl-N''-[2-[[(5-methyl-1H-imidazol-4-yl)methyl]thio]ethyl]guanidine
2-hydroxy-1,2,3-propanetricarboxylate bismuth (3+) complex (1:1) ("Cimetidine bismuth citrate")

To a solution of N-cyano-N'-methyl-N''-[2-[[(5-methyl-1H-imidazol-4-yl) methyl]thio]ethyl]guanidine (cimetidine, 2.52 ) in water (20 ml) at 90°-95° was added bismuth citrate (3.98 g) and the hot mixture stirred occasionally during 1 h. The suspension was filtered and the residue washed with water (5×10 ml), methanol (3×10 ml) and ether and dried to give unreacted bismuth citrate (1.628 g). The filtrate was evaporated to dryness in vacuo to give a white semi-solid. This was suspended in methanol (30 ml) and the mixture evaporated in vacuo. The residue was suspended in methanol (70 ml) and filtered and the residue washed well with methanol until free of cimetidine base then dried in vacuo to give the title compound (3.157 g.) T.l.c. (System A, 50:8:1) Rf zero (bismuth citrate) and Rf 0.35 (cimetidine);

Analysis Found: C,27.62;H,3.15;N,10.91;O,19.78;S,4.26. C$_{10}$H$_{16}$N$_6$S.1.2C$_6$H$_5$BiO$_7$,0.08C$_2$H$_5$OH,0.88H$_2$O requires C,27.82; H,3.26; N,11.21; O,19.98; S,4.28% Water assay indicated 2.37% H$_2$O =0.88 mol H$_2$O. N.m.r indicated 0.08 mol ethanol.

EXAMPLE 2

N-Cyano-N'-methyl-N''-[2-[[(5-Methyl-1H-imidazol-4-yl)methyl]thio]-ethyl]guanidine
[R-(R*,R*)]-2,3-dihydroxybutanedioate bismuth (3+) complex (1:1) ("Cimetidine bismuth tartrate")

A mixture of cimetidine (4.04 g) and bismuth tartrate (2.02 g) in water (15 ml) was warmed at approximately 90°-95° until solution was effected. The hot solution was filtered and the crystalline material which formed in the filter was washed well with hot water until most of the solid had passed the filter. The filtrate was evaporated to dryness in vacuo and the residue re-evaporated with methanol (2×50 ml). The solid residue was suspended in hot methanol (100 ml) and the mixture filtered. The residue was washed with methanol and then triturated with hot methanol. The mixture was filtered and the residue washed well with hot methanol then ether and dried to give the title compound (2.208 g). T.l.c. (System A 50:8:1) Rf 0.35 (cimetidine) and Rf zero (bismuth tartrate).

Analysis Found: C,27.00; H,3.33; N,13.01; O,17.49; S,4.81. C$_{10}$H$_{16}$N$_6$S.C$_4$H$_3$BiO$_6$,0.66H$_2$O, 0.17.CH$_3$OH requires C,27.20; H,3.38; N,13.43; O,17.46; S,5.12%. N.m.r. indicated 0.17 mol methanol. Water assay indicated 1.962% H$_2$O=0.66 mol H$_2$O.

EXAMPLE 3

1-Methyl-3-methylsulphonylmethyl-N-[3-[3-(1-piperidinylmethyl)phenoxy]propyl]-1H-1,2,4-triazole-5-amine 2-hydroxy-1,2,3-propanetricarboxylate bismuth (3+) complex (1:1.2) ("Sufotidine bismuth citrate")

A mixture of 1-methyl-3-methylsulphonylmethyl-N-[3-[3-(1-piperdinylmethyl)phenoxy]propyl]-1H-1,2,4-triazole-5-amine (sufotidine, 3.0 g) and bismuth citrate (2 g) in water (20 ml) was heated at 90°-98° until solution was effected (ca. 1 h). The viscous solution was filtered and the filtrate evaporated to dryness in vacuo. The residue was re-evaporated in vacuo with methanol (2×50 ml) and the residue extracted with methanol (80 ml) at 30°-40°. The supernatant liquid was decanted and, after filtration, was evaporated to dryness in vacuo to give a frothy solid (1). The pale-lemon residue left after decantation was extracted with boiling methanol (2×60 ml) and the decanted supernatants filtered to leave a small amount of insoluble residue (2) which was discarded. The combined filtrates (3) were evaporated to dryness and the residue dissolved in hot methanol (50 ml). The cloudy suspension was filtered through hyflo and the filtrate evaporated to dryness in vacuo to give a residue (4). Residues (1) and (4) were both extracted with boiling ethanol (70 ml×2) to give a residue which was triturated with ethanol to produce a fine suspension which was filtered off. The residue was washed well with ethanol at room temperature and dried in vacuo at 80°-85° to give the title compound (2.29 g). T.l.c. (System A 70:8:1) Rf 0.45 (sufotidine) and Rf zero (bismuth citrate).

Analysis Found: C,36.45; H,4.30; N,7.57; O,21.15; S,3.13. $C_{20}H_{31}N_5O_3S,1.2C_6H_5BiO_7,0.2C_2H_5OH,0.54 H_2O$ requires C,36.10; H,4.31; N,7.63; O,21.15; S,3.49% Water assay indicated 1.18% $H_2O$=0.5 mol $H_2O$ N.m.r. indicated ~1:1 ratio of sufotidine to bismuth citrate and 0.2 mol ethanol.

EXAMPLE 4

3-[[[2-[(Aminoiminomethyl)amino]-4-thiazolyl]methyl]-thio]-N-(aminosulphonyl)propanimidamide 2-hydroxy-1,2,3-propanetricarboxylate bismuth (3+) complex (1:1) ("Famotidine bismuth citrate").

To a stirred suspension of bismuth citrate (0.796 g) in water (8 ml) was added sufficient 0.88 aqueous ammonia to effect complete solution. The solution was filtered and the filtrate and washings evaporated to dryness in vacuo. The residue was re-evaporated with water (2×20 ml) and the residue dissolved in water (15 ml). The solution was heated at 90°-95° and to this was added a filtered solution of 3-[[[2-[(aminoiminomethyl)amino]-4-thiazolyl]methyl]thio]-N-(aminosulphonyl)-propanimidamide (famotidine, 0.674 g) in water (30 ml). The solution was evaporated to dryness in vacuo and the residue dried for 18 h under high vacuum. The solid residue was powdered and filtered off with the aid of ether and the residue dried at 85°-90° to give a solid (1.22 g). This was mixed with water (100 ml), the mixture heated on a steam bath and subjected to a steam of nitrogen for 4 h with periodic replacement of evaporated water. The suspension was evaporated to dryness in vacuo, the residue filtered off with the aid of ether and reduced to a powder and dried under high vacuum to give the title compound (1.046 g). T.l.c. (System A, 25:8:1) Rf 0.2 (famotidine) and Rf zero (bismuth citrate). N.m.r. δ(DMSO-d6) 2.49 (2H, t, SCH$_2$CH$_2$), 2.72 (2H, t, SCH$_2$CH$_2$), 3.67 (2H, s, SCH$_2$ring), 6.53 (2H, s, SO$_2$NH$_2$), 6.62 (1H, s, ring=CH) and 7.1 (4H, brs, C(NH$_2$)$_2$).

Example 5

1-Methyl-5-[[3-[3-(1-piperidinylmethyl)phenoxy]-propyl]amino]-1H-1,2,4-triazole-3-methanol 2-hydroxy-1,2,3-propanetricarboxylate bismuth (3+) complex (1:1)

To a suspension of bismuth citrate (3.98 g) in water (50 ml) was added sufficient 0.88 aqueous ammonia to dissolve the solid with the aid of gentle warming. The solution was filtered and the filter bed washed with water (2×10 ml). The solution was evaporated in vacuo to low bulk and the concentrated solution re-evaporated with water (70 ml ×5) until the solution and supernatant vapor was neutral to pH 1-14 paper. The residue was dissolved in water (100 ml) and 1-methyl-5-[[3-[3-(1-piperidinylmethyl)phenoxy]propyl]amino]-1H-1,2,4-triazole-3-methanol (Compound A, 3.59 g) added. The suspension was heated at 90°-95° until solution had been effected and an alkaline vapour (ammonia) was being evolved. The solution was filtered through Hyflo and the combined filtrate and washings evaporated in vacuo. The residue was re-evaporated with water (10×70 ml) and the resulting solid was dissolved in water (150 ml). The solution was heated to 90°-95° and a rapid stream of nitrogen passed through for 1.25 h. The solution was filtered through Hyflo and the filtrate evaporated to dryness in vacuo. The solid residue was then dried under high vacuum for 16 h, the solid residue suspended in dry ether, the suspension filtered and the residue dried under high vacuum at 80°-90° for 8 h to give the title compound (6.497 g).

Analysis Found: C,38.74; H,4.88; N,9.54; O,20.50. $C_{19}H_{29}N_5O_2.C_6H_5BiO_7.0.74$ $H_2O$ requires C,38,95; H,4.64; N,9.09; O,20.22%. Water assay indicated 1.76% w/w $H_2O$=0.094 mol %=0.74 mol. T.l.c. (System A, 50:8:1) Rf 0.40 (Compound A) and Rf zero (bismuth citrate).

EXAMPLE 6

N-[2-[[[2-[(Dimethylamino)methyl]-4-thiazoly]methyl]-thio]ethyl]-N'-methyl-2-nitro-1,1-ethenediamine 2-hydroxy-1,2,3-propanetricarboxylate bismuth (3+) complex (1:1) ("Nizatidine bismuth citrate")

To a suspension of bismuth citrate (3.98 g) in water (5 ml) was added 0.88 ammonia until all the solid had dissolved. The cloudy solution was filtered, and then evaporated to dryness in vacuo. The residue was re-evaporated with water (7×70 ml) to remove excess ammonia and N-[2-[[[2-[(dimethylamino)methyl]-4-thiazoly]methyl]thio]ethyl]-N'-methyl-2-nitro-1,1-ethenediamine (nizatidine, 3.98 g,) added to a solution of the residue in water (20 ml). The mixture was heated at 90°-95° until solution was effected and the resulting solution evaporated to dryness in vacuo. The residue was dissolved in water (70 ml) and re-evaporated in vacuo; the process being repeated four times. The solid residue which formed was recovered with the aid of ether and dried for 48 h at 80°-85° to give the title compound (7.0 g).

Analysis Found: C,29.28; H,3.78; N,10.29; O,21.11; S,8.40. $C_{18}H_{26}N_5O_9S_2Bi.0.1$ $H_2O$. 0.1 $C_6H_8O_7$. 0.3 $NH_3$ requires: C,29.56; H,3.72; N,9.82; O,20.75; S,8.49%.

The above analysis indicated the presence of 0.1 mole triammonium citrate and 0.1 mole $H_2O$, and the presence of 0.3 mole $NH_4^+$ was confirmed using the Merckoquant 10024 Ammonium Test Kit. Water assay indicated 0.17% $H_2O$=0.009 mol %=0.1 mole. T.l.c. (System A, 70:8:1) Rf 0.35 (nizatidine) and Rf zero (bismuth citrate).

The following Examples A to C illustrate pharmaceutical compositions according to the invention in which the active ingredient is in particular cimetidine bismuth citrate, famotidine bismuth citrate or nizatidine bismuth citrate. Other compounds according to the invention may be formulated in a similar manner, using an appropriate amount of active ingredient depending on the compound concerned, with suitable adjustments in the amounts of excipients and weights of the final dosage forms.

Example A Tablets

Tablets may be prepared by the normal methods such as direct compression or wet granulation.

The tablets may be film coated with suitable film forming materials, such as hydroxypropyl methylcellulose, using standard techniques.

| (a) | Direct Compression | mg/tablet |
|---|---|---|
| (i) | Famotidine Bismuth Citrate | 90.0 mg |
| | Lactose | 100.0 mg |
| | Microcrystalline Cellulose | 95.0 mg |
| | Cross-linked Polyvinylpyrrolidone | 12.0 mg |
| | Magnesium Stearate | 3.0 mg |
| | Compression weight | 300.0 mg |
| (ii) | Nizatidine Bismuth Citrate | 330.0 mg |
| | Lactose | 120.0 mg |
| | Microcrystalline Cellulose | 120.0 mg |
| | Cross-linked Polyvinylpyrrolidone | 24.0 mg |
| | Magnesium Stearate | 6.0 mg |
| | Compression weight | 600.0 mg |

The $H_2$-antagonist bismuth citrate, microcrystalline cellulose, lactose and cross-linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

Cimetidine bismuth citrate may be formulated in a similar manner, using 520.0 mg of the active ingredient and appropriate weights of the excipients to give a tablet compression weight of 900.0 mg.

| (b) | Wet granulation | mg/tablet |
|---|---|---|
| | Cimetidine Bismuth Citrate | 520.0 mg |
| | Lactose | 245.0 mg |
| | Pregelatinised Starch | 90.0 mg |
| | Cross-linked Polyvinylpyrrolidone | 36.0 mg |
| | Magnesium Stearate | 9.0 mg |
| | Compression weight | 900.0 mg |

The cimetidine bismuth citrate, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

Example B-Capsules

| (i) | | mg/capsule |
|---|---|---|
| (a) | Famotidine Bismuth Citrate | 90.0 mg |
| | Pregelatinised Starch | 108.0 mg |
| | Magnesium Stearate | 2.0 mg |
| | Fill weight | 200.0 mg |
| (b) | Nizatidine Bismuth Citrate | 330.0 mg |
| | Pregelatinised Starch | 66.0 mg |
| | Magnesium Stearate | 4.0 mg |
| | Fill weight | 400.0 mg |

The $H_2$-antagonist bismuth citrate and pregelatinised starch are screened through a 500 micron mesh sieve, blended together and lubricated with magnesium stearate (meshed through a 250 micron sieve). The blend is filled into hard gelatin capsules of a suitable size.

| | | mg/capsule |
|---|---|---|
| (ii) | Cimetidine Bismuth Citrate | 420.0 mg |
| | Lactose | 80.0 mg |
| | Polyvinylpyrrolidone | 22.0 mg |
| | Cross-linked Polyvinylpyrrolidone | 22.0 mg |
| | Magnesium Stearate | 6.0 mg |

| | mg/capsule |
|---|---|
| Fill weight | 550.0 mg |

The cimetidine bismuth citrate and lactose are blended together and granulated with a solution of polyvinylpyrrolidone. The wet mass is dried and milled. The magnesium stearate and cross-linked polyvinylpyrrolidone are screened through a 250 micron sieve and blended with the granule. The resultant blend is filled into hard gelatin capsules of a suitable size.

| Cimetidine Bismuth Citrate | 520.0 mg |
|---|---|
| Hydroxpropyl Methylcellulose | 45.0 mg |
| Propyl Hydroxybenzoate | 1.5 mg |
| Butyl Hydroxybenzoate | 0.75 mg |
| Saccharin Sodium | 5.0 mg |
| Sorbitol Solution | 1.0 ml |
| Suitable Buffers | qs |
| Suitable Flavours | qs |
| Purified Water to | 10.0 ml |

The hydroxypropyl methylcellulose is dispersed in a portion of hot purified water together with the hydroxybenzoates and the solution is allowed to cool to room temperature. The saccharin sodium, flavours and sorbitol solution are added to the bulk solution. The cimetidine bismuth citrate is dissolved in a portion of the remaining water and added to the bulk solution. Suitable buffers may be added to control the pH in the region of maximum stability. The solution is made up to volume, filtered and filled into suitable containers.

Syrups containing famotidine bismuth citrate or nizatidine bismuth citrate as the active ingredient may be prepared in a similar manner, replacing cimetidine bismuth citrate with famotidine bismuth citrate (90.0 mg) or nizatidine bismuth citrate (330.0 mg).

I claim:

1. A salt formed between a basic histamine $H_2$-receptor antagonist and a complex of bismuth with a carboxylic acid, or a solvate of such a salt, wherein said carboxylic acid comprises a carboxyl group which is available for salt formation with said basic histamine $H_2$-receptor antagonist and three additional functional groups selected from carboxyl and hydroxyl groups in the molecule for reaction with bismuth, said basic histamine $H_2$-receptor antagonists having basic functionality for reaction with the carboxyl group of the complex to form said salt; and said basic $H_2$-receptor antagonist containing a functionality selected from the group consisting of imidazole, aminoalkylbenzene, aminoalkylfuran, aminoalkylthiazole, guanidinothiazolyl and guanidino pyrazolyl with the proviso that said basic $H_2$-receptor antagonist is not ranitidine.

2. A salt as claimed in claim 1, prepared by reacting a basic $H_2$-receptor antagonist with a bismuth carboxylic acid complex.

3. A salt as claimed in claim 1, wherein the carboxylic acid is citric acid, tartaric acid, ethylenediaminetetraacetic acid, propylcitric acid or agaricic acid.

4. A salt as claimed in claim 1, wherein the carboxylic acid is citric acid or tartaric acid.

5. A salt formed between a basic histamine $H_2$-receptor antagonist and a complex of bismuth with a carboxylic acid, or a solvate of such a salt, wherein said carboxylic acid contains a carboxyl group which is available for salt formation with said basic histamine $H_2$- receptor antagonist and three additional functional groups selected from the group consisting of carboxyl and hydroxyl groups in the molecule for reaction with bismuth, and said basic histamine $H_2$-receptor antagonist having basic functionality for reaction with the carboxyl group of the complex to form said salt; and said basic $H_2$-receptor antagonist being selected from the group consisting of cimetidine, sufotidine, famotidine, roxatidine, niperotidine, nizatidine, mifenfidine, zaltidine, ebrotidine, bisfentidine, 1-methyl-5-[[3-[3-(1-piperidinylmethyl)phenoxy]propyl]amino]-1H-1,2,4-triazole-3-methanol,3-amino-4-[[3-[3-(1-piperidinylmethyl)phenoxyl]-propyl]amino-3-cyclobutene-1,2-dione and 5-[3-[2-(2,2,2-trifluoroethyl)-guanidino]pyrazol-1-yl]valeramide.

6. A salt as claimed in claim 5, wherein the carboxylic acid is citric acid, tartaric acid, ethylenediaminetetraacetic acid, propylcitric acid or agaricic acid.

7. A salt as claimed in claim 5, wherein the basic histamine $H_2$-receptor antagonist is selected from cimetidine, sufotidine, famotidine and nizatidine.

8. A salt as claimed in claim 5, wherein the carboxylic acid is citric acid or tartaric acid.

9. A salt as claimed in claim 5, prepared by reacting a basic $H_2$-receptor antagonist with a bismuth carboxylic acid complex.

10. N-cyano-N'-methyl-N''-[2-[[(5-methyl-1H-imidazol-4-yl)methyl]thio]ethyl]guanidine 2-hydroxy-1,2,3-propanetricarboxylate bismuth (3+) complex;

N-cyano-N'-methyl-N''-[2-[[(5-methyl-1H-imidazol-4-yl)methyl]thio]ethyl]guanidine [R-(R*R*)]-2,3-dihydroxybutanedioate bismuth (3+) complex;

1-methyl-3-methylsulphonylmethyl-N-[3-[3-(1-piperidinylmethyl)phenoxy]propyl]-1H-1,2,4-triazole-5-amine 2-hydroxy-1,2,3-propanetricarboxylate bismuth (3+) complex; 3-[[[2-[(aminoiminomethyl)amino]-4-thiazolyl]methyl]-thio]-N-(aminosulphonyl)propanimidamide 2-hydroxy-1,2,3-propanetricarboxylate bismuth (3+) complex;

N-[2-[[[2-[(dimethylamino)methyl]-4-thiazolyl]methyl]thio]ethyl]-N'-methyl-2-nitro-1,1-ethenediamine 2-hydroxy-1,2,3-propanetricarboxylate bismuth (3+) complex;

or solvates thereof.

11. A pharmaceutical composition for the treatment of gastrointestinal disorders which comprises an effective amount for the treatment of said disorder of a salt as claimed in claim 1, together with at least one pharmaceutically acceptable carrier or diluent.

12. A pharmaceutical composition for the treatment of gastrointestinal disorders which comprises an effective amount for the treatment of said disorder of a salt as claimed in claim 5, together with at least one pharmaceutically acceptable carrier or diluent.

* * * * *